(12) United States Patent
Luke et al.

(10) Patent No.: US 7,275,636 B2
(45) Date of Patent: Oct. 2, 2007

(54) TRANSPORT ROLLER SUSPENSION

(75) Inventors: John George Luke, Bristol (GB); Richard Sleeman, Bristol (GB)

(73) Assignee: Mass Spec Analytical Ltd., Bristol (GB)

( * ) Notice: Subject to any disclaimer, the term of this patent is extended or adjusted under 35 U.S.C. 154(b) by 0 days.

(21) Appl. No.: 11/098,982

(22) Filed: Apr. 5, 2005

(65) Prior Publication Data
US 2005/0217968 A1  Oct. 6, 2005

(30) Foreign Application Priority Data
Apr. 6, 2004  (EP) .................................. 04252044

(51) Int. Cl.
*B65G 29/00*  (2006.01)
(52) U.S. Cl. ...................................... 198/624
(58) Field of Classification Search ............... 198/624; 271/274
See application file for complete search history.

(56) References Cited

U.S. PATENT DOCUMENTS

| | | | | |
|---|---|---|---|---|
| 4,170,350 A | * | 10/1979 | Conti | 271/274 |
| 4,195,832 A | * | 4/1980 | Krumrey | 271/274 |
| 4,431,179 A | * | 2/1984 | Westover et al. | 271/274 |
| 4,613,127 A | * | 9/1986 | Wishart et al. | 271/274 |
| 4,620,807 A | * | 11/1986 | Polit | 400/56 |
| 4,705,413 A | * | 11/1987 | Arnoldi et al. | 400/56 |
| 5,426,497 A | * | 6/1995 | Morganti et al. | 399/394 |
| 5,474,289 A | * | 12/1995 | Pilling | 271/265.04 |

FOREIGN PATENT DOCUMENTS

| | | | | |
|---|---|---|---|---|
| GB | 2363517 A | * | 12/2001 | |
| JP | 04072246 A | * | 3/1992 | 271/274 |

* cited by examiner

*Primary Examiner*—Mark A Deuble
(74) *Attorney, Agent, or Firm*—Gardere Wynne Sewell LLP

(57) ABSTRACT

A transport roller suspension mechanism for supporting at least one transport roller of a sample transport mechanism for introducing a substantially planar sample carrier to a chemical analysis device, the transport roller mechanism comprising: a suspension block arranged to be pivotally connected to a fixed portion of the sample transport mechanism and being arranged to rotatably receive one end of a transport roller shaft; and a biasing member arranged to be resiliently urged against the suspension block.

6 Claims, 4 Drawing Sheets

TRANSPORT ROLLER SUSPENSION

BACKGROUND TO THE INVENTION

The ability to accurately and reliably determine the presence or otherwise of a particular compound on an everyday object is of significant importance to customs and police forces around the world. The compounds of highest interest include illicit drugs and explosives and it is their detection in both a forensic context and with regards to the detection of contraband or tariff evasion that is of interest to police and custom forces respectively. Generally, the compounds of interest are likely to be present only in extremely small, or trace, amounts. Consequently, extremely sensitive chemical analysis techniques are employed to determine the presence or otherwise of a particular compound.

One such analytical approach known from the prior art is to use a tandem mass spectrometer to chemically analyse a collected sample. Traditional techniques for the preparation of the samples prior to analysis by the mass spectrometer typically include complex and time consuming purification and chemical treatment steps involving the use of solvents and glassware. The sample preparation techniques inhibit the use of tandem mass spectrometers as part of a "real-time" security process, such as a part of the security checks applied to a traveller prior to boarding an aeroplane.

In UK patent application GB 2363517 A, the current applicants discuss the introduction of a sample to a mass spectrometer by heating a sheet-like carrier, such as a bank note or an aeroplane ticket, within a confined space between two heated bodies such that a sufficient quantity of substance is desorbed from the carrier to be passed directly into the ionisation chamber of a mass spectrometer for analysis. The use of a carrier transport system involving pairs of rollers to enable a number of separate carriers to be analysed in succession is also discussed.

U.S. Pat. No. 4,705,413 discloses a roller mechanism for compensating for thickness of pieces of mail in a mailing machine. A reaction (idle) roller is provided with a single suspension element acting on the centre of the idle roller. There is no disclosure of surmounting the problems associated with providing suspension for driven rollers.

It is to improvements in the transport system for the analysis apparatus that this present application relates.

SUMMARY OF THE INVENTION

According to a first aspect of the present invention there is provided a transport roller suspension mechanism for supporting at least one rotatably driven transport roller of a sample transport mechanism for introducing a substantially planar sample carrier to a chemical analysis device, the transport roller suspension mechanism comprising: a pair of suspension blocks arranged to be pivotally connected to a fixed portion of the sample transport mechanism and being arranged to rotatably receive opposite ends of the rotatably driven transport roller shaft; and a biasing member arranged to be resiliently urged against the suspension block.

Preferably, the biasing member is slidably received within a correspondingly shaped recess in a fixed housing element. The biasing member may additionally be resiliently urged towards the suspension block by means of a spring element located in the recess in the fixed housing.

Additionally or alternatively, the biasing member may comprise an elongate plunger.

Additionally or alternatively, the pivot point of the suspension block and the axis of rotation of the transport roller may be longitudinally displaced from one another such that pivotable movement of the suspension block causes the transport roller to move in an arc.

Preferably, the transport rollers may have a plurality of circumferential ridges formed thereon, the circumferential ridges of each roller within a pair of rollers being aligned with one another.

BRIEF DESCRIPTION OF THE DRAWINGS

Embodiments of the present invention will now be described, by means of illustrative example only, with reference to the accompanying figures, of which.

DESCRIPTION OF PREFERRED EMBODIMENTS OF THE INVENTION

Figure 1:
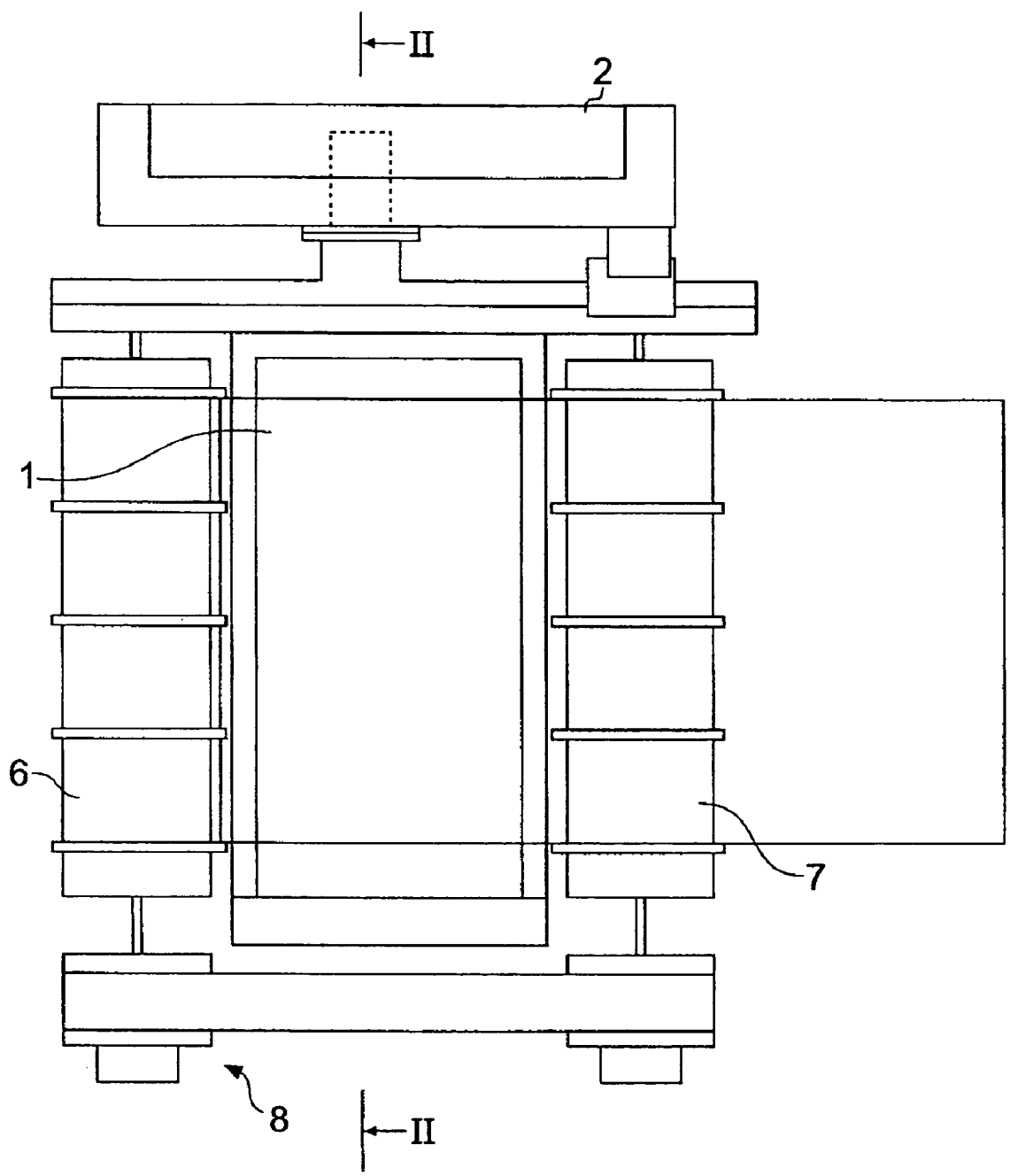
FIG. 1 is a plan view of an analytical apparatus having a roller transport mechanism.
Figure 2:
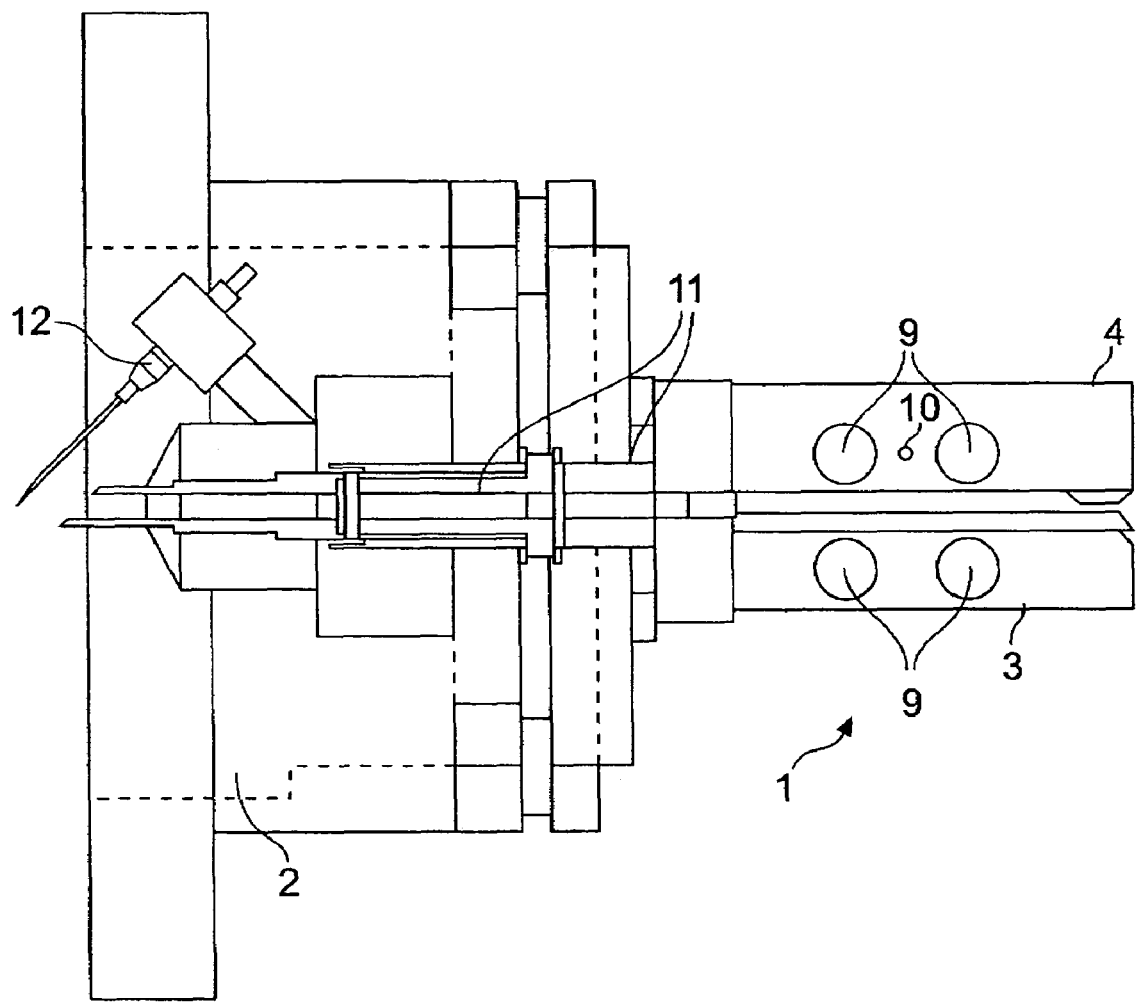
FIG. 2 is a partial sectional view through the apparatus on the line II-II of FIG. 1.

Referring to FIG. 1, a chemical analysis apparatus of the general kind described in the applicant's earlier UK application GB 2363517 is shown in plan view. The apparatus comprises a desorption chamber 1 and a plenum chamber 2 (shown only in part) that is associated with a conventional chemical ionisation mass spectrometer (not shown). The desorption chamber 1 comprises first and second heated blocks 3, 4, as can be seen in FIG. 2, arranged in a closely-spaced parallel relationship separated by a desorption envelope 5. The desorption envelope 5 is arranged to receive a planar carrier that, by way of example, may comprise any chemically inert and absorbent thin sheet material such as a card or blotting paper, or other similar planar carrier such as a banknote, or plane or train ticket or boarding pass. The carrier may be fed into the desorption envelope 5 by any suitable means. In the example shown in FIG. 1, pairs of transportation rollers 6 and 7 are provided on opposite sides of the blocks 4 and 5 for moving the carrier through the desorption envelope 5 in the nip of the rollers. The rollers may be driven by a variable speed electric motor via suitable gearing, or a combination of gearing and drive belts, as indicated generally at 8 in FIG. 1.

The heated blocks 3 and 4 are heated by one or more electrical resistance type cartridge heaters 9, as shown in FIG. 2. A thermocouple temperature sensor 10 is also inserted in the upper block 4 and provides negative feedback to maintain the blocks at a minimum temperature. A brass transfer line 11 is connected to the desorption chamber 1 and is in flow communication with the desorption envelope 5, thus providing a transfer passage that leads directly into the plenum chamber 2 of the mass spectrometer. The plenum chamber is maintained at a reduced pressure relative to the desorption envelope 5 so that desorbed substances are thereby drawn through the brass transfer line and passed directly into the plenum chamber 2. Adjacent to the exit end of the transfer line there is disposed a high voltage electrode 12 (e.g. at 8 kV). The corona discharge causes immediate ionisation of any substances entering the plenum chamber for analysis by the mass spectrometer in known manner. Other ionisation techniques could also be used.

Figure 3:
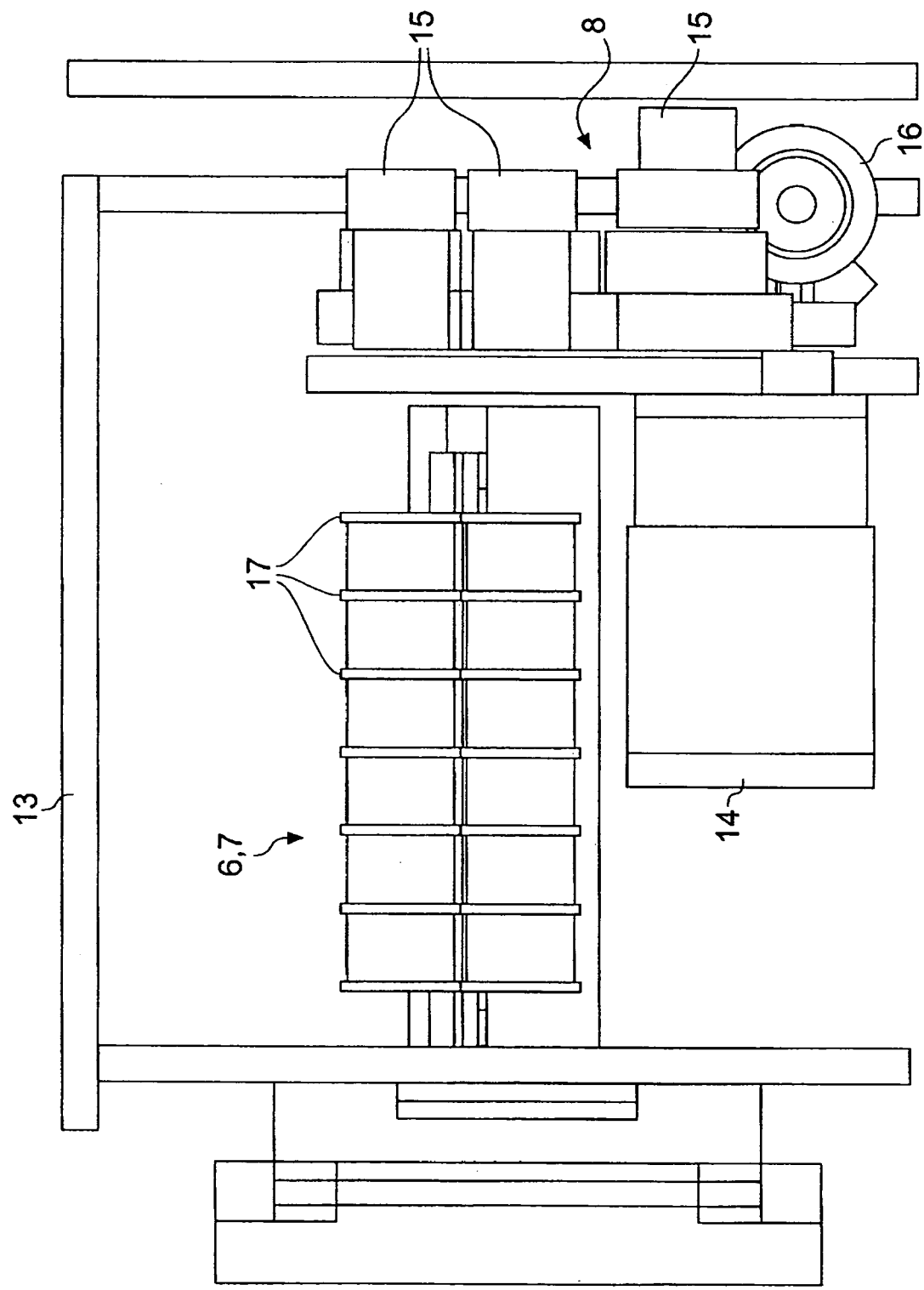
FIG. 3 is a side elevation view of the transport mechanism in accordance with an embodiment of the present invention.

With reference to FIG. 3, the transport roller mechanism comprises a frame 13 that supports the pairs of rollers 6 and 7, the drive mechanism 8 and electric motor 14. Each of the individual rollers is carried by a respective roller shaft that is rotatably mounted to the frame 13. Mounted to one end of the roller shafts are an arrangement of intermeshing gears 15 that in turn engage with a worm shaft 16. The worm shaft 16 is driven by a further appropriate gear arrangement from a DC electric stepper motor 14. The gear arrangement is provided such that each individual roller is driven so as to convey a carrier through the desorption envelope 5 of the desorption chamber 1. The worm shaft 16 is provided in preferred embodiments, in preference over other gearing or belt drive arrangements, as it has been found that the use of a belt drive with a belt running from the first pair of rollers 6 to the second pair of rollers 7 causes a significant bending moment to be applied to the ends of the roller shafts. The slight bending of the roller shafts that this can cause is detrimental to the consistent transport of the carriers through the desorption chamber 1. It has also been found that a worm drive arrangement permits a higher throughput rate of carriers.

The use of a DC stepper motor 14 allows the carrier to be held stationary within the desorption chamber 1 for a preprogrammed period of time, thereby maximising the absorption of any sample products carried on the carrier. The operation of the stepper motor 14 may be controlled in conjunction with one or more sensors, such as a photo detector, arranged to determine the position of a carrier within the transport mechanism and therefore within the desorption chamber 1. Further sensors may be provided to ensure that a carrier has fully exited the desorption chamber 1 before a subsequent carrier is transported via the rollers into the desorption chamber. The transport rollers are preferably capable of being reversed, either manually or automatically, in the event of either a carrier becoming jammed in the desorption chamber or the gear train 8 itself becoming jammed.

The rollers preferably have a plurality of raised ridges 17 formed thereon, with the ridges formed on upper and lower rollers of each roller pair being aligned with one another. Consequently, it is in fact only the ridges 17 of the rollers that come into contact with the sheet carrier as it is fed through by the rotation of the rollers. The remaining areas of the carrier are in fact not brought into contact with the rollers at any point. This therefore minimises the possibility of a substance of interest being deposited on the rollers from a first carrier and subsequently deposited from the rollers onto a subsequent carrier, thereby cross contaminating the individual carriers.

In some embodiments of the present invention the carrier path through the transport mechanism may be divided, for example by providing a lateral barrier positioned at a point along the length of the transport rollers. Two separate transport paths through the desorption chamber 1 are thus provided allowing two sample carriers to be passed through the desorption chamber 1 at a time, thereby doubling the throughput of the detection apparatus as a whole. In preferred embodiments both carrier 'lanes' pass through the same desorption chamber, so that a positive result may be produced even if only one of the carriers is contaminated. However, it will be appreciated by those skilled in the art that separate desorption envelopes 5 for each carrier path may be provided, or two separate transport mechanisms and associated desorption apparatus, if the particular application merited the increased complexity and cost.

Figure 4:
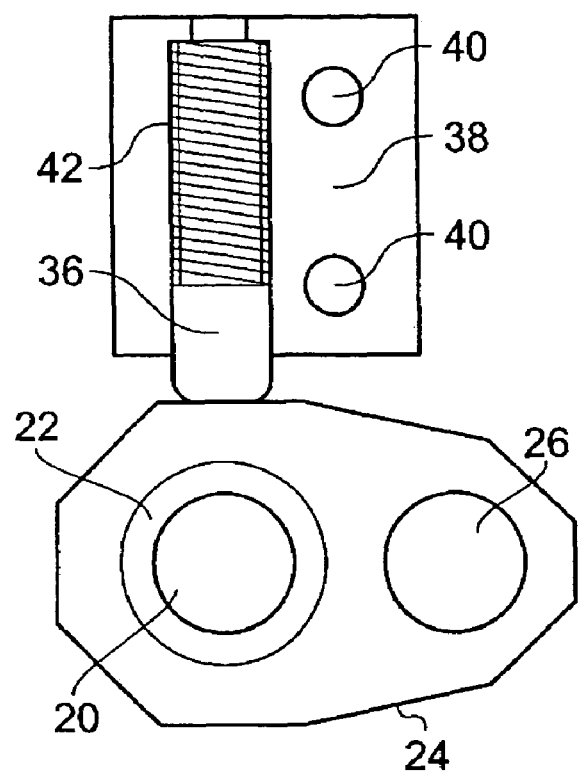
FIG. 4 is a sectional view of a roller transport suspension mechanism according to an embodiment of the present invention.
Figure 5:
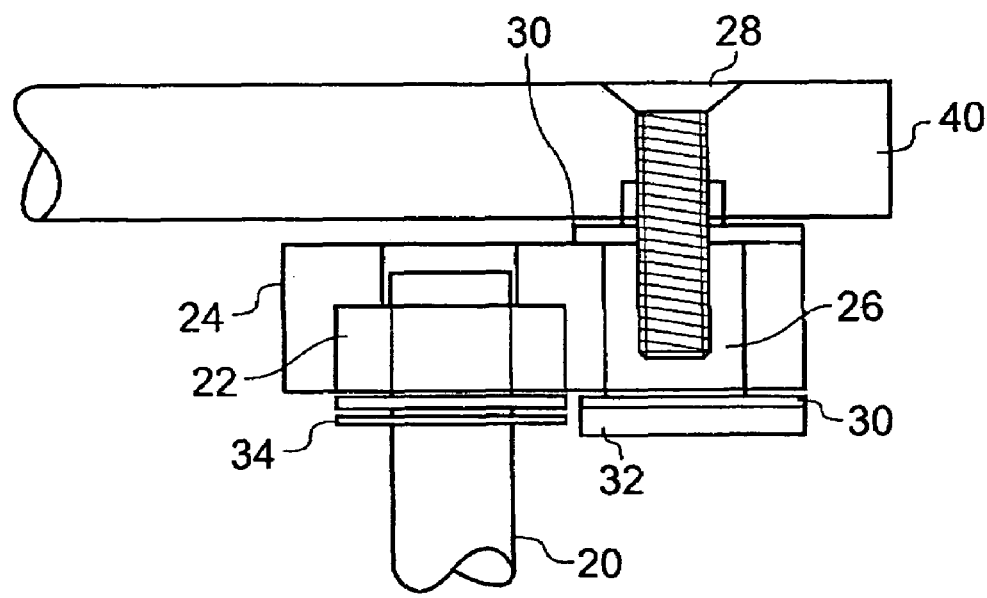
FIG. 5 is a plan view of the roller transport suspension mechanism of FIG. 4.

To allow for carriers of differing thicknesses to be efficiently transported by the pairs of rollers 6 and 7, and to minimise the likelihood of a carrier not travelling through the transport arrangement in a straight line, it is preferred that at least one of each pair of rollers is provided with some means of suspension. A preferred means of suspension according to embodiments of the present invention is illustrated in FIGS. 4 and 5. FIGS. 4 and 5 illustrate in front elevation and plan view respectively a suspension arrangement for the upper roller of each of the roller pairs, although the lower roller of each pair may be suspended in an analogous fashion. The suspension arrangement shown in FIGS. 4 and 5 is provided at both ends of each upper roller shaft. The roller shaft 20 is mounted in a bearing housing 22 that is in turn mounted within a suspension block 24. As can be best seen from FIG. 5, the suspension block 24 is pivotally mounted on the frame 13 of the transport arrangement. The suspension block 24 is pivotally mounted by means of a brass pivot bearing shaft 26 that is secured, for example by means of a screw 28, to the frame body 13. The suspension block 24 can therefore pivot about the bearing shaft 26, thereby allowing the roller mounted on the roller shaft 20 a degree of vertical movement. Washers 30 are provided between the suspension block 26 and the frame 13 and between the suspension block and the pivot bearing shaft 26, with a further washer 32 being provided on the roller shaft 20 and held in place by means of a circlip 34 secured to the roller shaft 20.

As shown in FIG. 4, the suspension block 24 is in contact with a plunger 36 slidably housed within a mounting block 38 that is secured to the frame 13 by means of the securing holes 40. The plunger 36 is slidably housed within a cylindrical shaft formed within the mounting block 38, the cylindrical shaft having either a blind end, or having an inwardly extending shoulder, or flange, at the opposite end of the shaft from which the plunger 36 protrudes. The plunger 36 also has a shoulder formed thereon towards one end of its length, thus allowing a helical spring to be mounted within the shaft, with one end of the helical spring bearing against the blind end or shoulder of the shaft and the opposite end of the spring bearing against the shoulder on the plunger. In this way, the plunger 36 is resiliently biased against the suspension block 24, thus urging the suspension block 24, and therefore the roller mounted thereon, towards the second of the relative pair of rollers. The upper roller is therefore biased towards the lower roller yet is still able to travel through a degree of vertical movement relative to the second roller.

It would be appreciated that other biasing means may be provided in place of the helical spring 42 to urge the plunger 36 against the suspension block 24. Alternative spring arrangements may also be provided, such as a torsion spring mounted around the pivot bearing shaft 26 on which the suspension block pivots, or other analogous means.

The transport mechanism is constructed from materials, and arranged in such a manner, that allow it to continuously function in a reliable manner for extended periods of time, such as several hours, when subjected to the elevated desorption temperatures that are typically in the range of 100 to 350° C.

The invention claimed is:

1. A transport mechanism for introducing a substantially planar sample carrier to a chemical analysis device, the transport mechanism comprising at least one pair of transport rollers and a roller suspension mechanism on which at least a first one of the transport rollers of the at least one pair of transport rollers is mounted, the first transport roller being rotatably driven, the suspension mechanism comprising:
   a pair of suspension blocks pivotally connected to a fixed portion of the transport mechanism and being arranged to rotatably receive opposite ends of a rotatably driven transport roller shaft; and
   a pair of biasing members each in engagement with a respective suspension block, each biasing member being resiliently urged towards the respective suspension block.

2. The transport mechanism according to claim 1, wherein each biasing member is slidably received within a respective correspondingly shaped recess in a fixed housing element.

3. The transport mechanism according to claim 2, wherein each biasing member is resiliently urged towards the respective suspension block by means of a spring element located in the respective recess in the fixed housing.

4. The transport mechanism according to claim 1, wherein each biasing member comprises an elongate plunger.

5. The transport mechanism according to claim 1, wherein the pivot point of the suspension block and the axis of rotation of the rotatably driven transport roller are longitudinally displaced from one another such that pivotal movement of the suspension block causes the transport roller received therein to move in an arc.

6. The transport mechanism according to claim 1, wherein each transport roller has a plurality of circumferential ridges formed thereon, the circumferential ridges of each roller within a pair of rollers being aligned with one another.

* * * * *